(12) United States Patent
Darwinkel et al.

(10) Patent No.: US 9,126,345 B2
(45) Date of Patent: Sep. 8, 2015

(54) DOMESTIC APPLIANCE COMPRISING MEANS FOR GENERATING ELECTRIC ENERGY IN A FUNCTIONAL ACTION UNIT

(75) Inventors: Geert-jan Darwinkel, Eindhoven (NL); Mattheus Jacobus Van Der Meer, Eindhoven (NL); Pascal Homan, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 919 days.

(21) Appl. No.: 12/993,123

(22) PCT Filed: May 20, 2009

(86) PCT No.: PCT/IB2009/052115
§ 371 (c)(1),
(2), (4) Date: Nov. 17, 2010

(87) PCT Pub. No.: WO2009/147561
PCT Pub. Date: Dec. 10, 2009

(65) Prior Publication Data
US 2011/0067243 A1  Mar. 24, 2011

(30) Foreign Application Priority Data
May 27, 2008  (EP) .................................. 08156956

(51) Int. Cl.
*B26B 19/38* (2006.01)
*B26B 19/14* (2006.01)
*A61C 17/22* (2006.01)

(52) U.S. Cl.
CPC ............. *B26B 19/14* (2013.01); *B26B 19/3873* (2013.01); *A61C 17/22* (2013.01)

(58) Field of Classification Search
CPC ........................... B26B 19/14; B26B 19/3873
USPC ......... 30/43.5, 43.6, 43.8, 43.9, 43.91, 43.92, 30/45
See application file for complete search history.

(56) References Cited

U.S. PATENT DOCUMENTS

| 1,538,992 | A |   | 5/1925  | Hopkins |
|-----------|---|---|---------|---------|
| 2,222,308 | A | * | 11/1940 | Bott .............................. 30/43.6 |
| 2,279,682 | A | * | 4/1942  | Jackson ......................... 30/43.6 |
| 2,301,147 | A | * | 11/1942 | Schaaf et al. ..................... 30/45 |
| 2,383,421 | A | * | 8/1945  | Schultz ........................... 607/94 |
| 3,027,507 | A | * | 3/1962  | Hubner .......................... 320/111 |
| 3,141,239 | A | * | 7/1964  | Meyer et al. ................. 30/34.05 |
| 3,257,599 | A | * | 6/1966  | Tolmie et al. ................. 320/115 |

(Continued)

FOREIGN PATENT DOCUMENTS

| JP | 53-63154   | * | 6/1978 |
| WO | 0234482 A1 |   | 5/2002 |

(Continued)

*Primary Examiner* — Hwei C Payer

(57) ABSTRACT

A domestic appliance includes a functional action unit which has at least one movably arranged member, and a generator configured to generate electric energy at the location of the functional action unit. The generator is associated with the movably arranged member, and employs movement of this member in a process of generating electric energy. The generator includes a permanent magnet and an electric coil, where the magnet may be mounted on the movably arranged member. By having the generator at a location inside the functional action unit, it is possible to have one or more electric components at a location inside this unit without the need for external electric connections.

18 Claims, 4 Drawing Sheets

(56) References Cited

U.S. PATENT DOCUMENTS

| | | | |
|---|---|---|---|
| 3,298,101 A * | 1/1967 | MacCarthy | 30/43.5 |
| 3,675,324 A * | 7/1972 | Yamada et al. | 30/43.6 |
| 3,756,105 A * | 9/1973 | Balamuth et al. | 83/14 |
| 3,797,109 A * | 3/1974 | Yamada et al. | 30/43.6 |
| 6,226,870 B1 * | 5/2001 | Barish | 30/43.6 |
| 7,015,602 B2 * | 3/2006 | Kraus et al. | 310/36 |
| 7,288,863 B2 * | 10/2007 | Kraus | 310/37 |
| 7,504,751 B2 * | 3/2009 | Kraus et al. | 310/12.04 |
| 8,127,453 B2 * | 3/2012 | Haczek et al. | 30/43.92 |
| 2002/0108251 A1 * | 8/2002 | Brum et al. | 30/43.7 |
| 2004/0194316 A1 | 10/2004 | Lin et al. | |
| 2006/0281042 A1 | 12/2006 | Rizoiu et al. | |
| 2007/0030671 A1 | 2/2007 | Long et al. | |
| 2007/0137043 A1 * | 6/2007 | Kraus et al. | 30/43.9 |
| 2007/0177377 A1 | 8/2007 | Ding et al. | |
| 2011/0099814 A1 * | 5/2011 | Fuerst et al. | 30/34.05 |

FOREIGN PATENT DOCUMENTS

| | | | | |
|---|---|---|---|---|
| WO | 2006067710 A1 | | 6/2006 | |
| WO | WO 2007/033730 | * | 3/2007 | B26B 19/38 |

* cited by examiner

DOMESTIC APPLIANCE COMPRISING MEANS FOR GENERATING ELECTRIC ENERGY IN A FUNCTIONAL ACTION UNIT

FIELD OF THE INVENTION

The present invention relates to a domestic appliance comprising a unit for performing an action which is directly related to an intended function of the appliance, and at least one movably arranged member which is located in the functional action unit. Furthermore, the present invention relates to a unit for use in an appliance as mentioned, said unit being adapted to perform an action which is directly related to an intended function of the appliance, and comprising at least one movably arranged member.

BACKGROUND OF THE INVENTION

An example of a domestic appliance as mentioned in the opening paragraph is an appliance which is adapted to perform a shaving process, i.e. a process of removing hairs from skin by cutting through the hairs at a position close to the skin, and which comprises a shaving unit having at least one cutting member. Such a shaving appliance is known, for example, from WO 2006/067710. Besides the shaving unit, the known shaving appliance comprises a handle. The shaving unit of the known shaving appliance comprises three rotatably arranged cutting members in a triangular formation. The cutting members are driven by a single shaft which protrudes from the handle, and which is positioned centrally with respect to the cutting members. Furthermore, the drive shaft is driven by a motor which is accommodated in the handle, possibly together with suitable transmission and/or reduction means.

In one embodiment of the known shaving appliance, each cutting member is provided with a gear wheel at one side, and the drive shaft is provided with a primary gear wheel which is arranged to engage the respective gear wheels of the cutting members. In this way, it is achieved that upon rotation of the drive shaft, the primary gear wheel of the drive shaft will drive the gear wheels of the cutting members, thereby rotating the cutting members.

It is desirable to have a shaving unit which is equipped with other components besides the cutting members, in particular electric components for performing peripheral functions. A well-known example of such components is a number of light emitting diodes (LEDs) for emitting ultra violet rays for killing germs which are present in the shaving unit, especially on the cutting members. In this respect, it is noted that it is known from US 2004/0194316 to have per cutting member a plurality of LEDs which are located on a top surface of the handle and around a drive shaft protruding from the handle. However, providing the shaving appliance known from WO 2006/067710 with LEDs in this way would not yield much effect, as a structure for supporting the cutting members would very much hinder the ultra violet rays on their way to the cutting members.

SUMMARY OF THE INVENTION

It is an object of the present invention to solve the above-sketched problem. Among other things, the present invention provides a way for having an optimum germ-killing functionality in a shaving appliance, such as the shaving appliance known from WO 2006/067710, by providing means for generating electric energy at the location of a functional action unit of an appliance, which means are associated with a movably arranged member which is located in the unit, and are adapted to employ movement of this member in a process of generating electric energy, and by having at least one electric component which is located in the functional action unit, and which is adapted to using electric energy generated by said means for its operation.

According to an insight underlying the present invention, the movement of at least one movably arranged member which is located in the functional action unit can suitably be used for generating electric energy, so that it is possible to realize a source for providing electric energy inside the unit. Hence, when it is desirable to have one or more electric components in an appliance, wherein a position inside the functional action unit would be an optimal position of these components, it is possible to arrange the components accordingly, without a need for an electric cord or the like extending from the components to an electric connection point outside of the unit.

In many practical cases, the movably arranged member is driven mechanically, wherein the energy needed to perform the driving action is generated by a device such as an electric motor which is suitable for transforming electric energy to mechanical energy. Normally, such a device is arranged outside of the functional action unit. By applying the invention, it is achieved that electric energy may be obtained in the functional action unit by transforming mechanical energy back to electric energy at the location of the unit. As an advantageous result, there is no need to use complex seals or the like on moving elements, which would be the case if there was no intermediate transformation to mechanical energy.

The creation of a source providing electric energy inside the functional action unit on the basis of movement of at least one movably arranged member which is located in the unit does not only offer the possibility of having LEDs arranged inside the unit. Other electric components may be provided as well. For example, when the functional action unit is a shaving unit, other electric components may be components for retaining and releasing a lid of a structure for accommodating a cutting member, micro heating components, micro cooling components, a light source in order to visualize a moving cutting member in a stroboscopic manner, a light source in order to visualize a cleaning process of the shaving unit which is performed by using cleaning fluid, components suitable to be used at locations where drying of difficult-to-reach areas needs to be performed, and integrated circuits (ICs) for wireless communication purposes from the shaving unit to the handle of the shaving appliance or to a device for subjecting the unit to a cleaning action.

The movably arranged member whose movement is used in a process of generating electric energy may be a movable member of driving means which are located in the functional action unit, and which are adapted to impose a movement on at least one member for performing the action which is directly related to the intended function of the appliance, which is also located in the functional action unit. In a practical case, the driving means may comprise a rotatably arranged gear wheel. It is advantageous if at least one member of the means for generating electric energy is attached to the gear wheel, so that this member may be rotated along with the gear wheel. For example, the functional action unit comprises at least two functional action members, wherein the gear wheel has a central position between the functional action members and serves for driving all functional action members.

In a practical embodiment of the appliance according to the present invention, the means for generating electric energy comprise a permanent magnet and an electric coil, i.e. a coil comprising wound electrically conductive wires. It is a well-known fact that it is possible to induce electric energy by subjecting an electric coil to an alternating magnetic field. For example, the permanent magnet may be attached to a movable member of the driving means, so that the magnet is arranged to be movable as well. This magnet may be arranged such as to extend through an electric coil, but it is also possible that the magnet is arranged in the vicinity of one or more electric coils inside of which another permanent magnet is arranged, in a manner known per se. In any case, at least one permanent magnet and at least one electric coil may be used to generate the electric energy as desired on the basis of known physical principles.

Like many known appliances, the appliance according to the present invention may further comprise a handle which is intended to be taken hold of by a user during intended application of the appliance, and which encloses means for providing power to the movably arranged member with which the means for generating electric energy are associated, wherein the functional action unit is mounted on the handle. In a practical embodiment, the appliance according to the present invention comprises a drive shaft protruding from the handle and extending into the functional action unit.

In case the appliance according to the present invention is a shaving appliance, this may be of the type which is adapted to perform a shaving process by using rotating cutting members, like the shaving appliance known from WO 2006/067710. In that case, at least one member of the means for generating electric energy may be rotatably arranged, like the cutting members. However, within the scope of the present invention, it is also possible that the shaving appliance is of another type, in particular a type which is adapted to perform a shaving process by using reciprocating cutting members, wherein at least one member of the means for generating electric energy is arranged such as to be capable of performing a reciprocating movement as well.

The present invention also relates to a unit which is suitable to be used in the above-described appliance, i.e. a unit adapted to perform an action which is directly related to an intended function of the appliance, and comprising at least one movably arranged member, means for generating electric energy, which are associated with the movably arranged member, and which are adapted to employ movement of this member in a process of generating electric energy, and at least one electric component which is adapted to using electric energy generated by said means for its operation.

The above-described and other aspects of the present invention will be apparent from and elucidated with reference to the following description of a shaving appliance according to the present invention, and in particular a shaving unit which is part of this shaving appliance. For the sake of completeness, it is noted that the fact that the invention will be explained in the context of an appliance which is adapted to perform a shaving process should not be understood such as to imply that the invention is limited to this context.

BRIEF DESCRIPTION OF THE DRAWINGS

The present invention will now be explained in greater detail with reference to the Figures, in which equal or similar parts are indicated by the same reference signs, and in which.

DETAILED DESCRIPTION OF EMBODIMENTS

Figure 1:
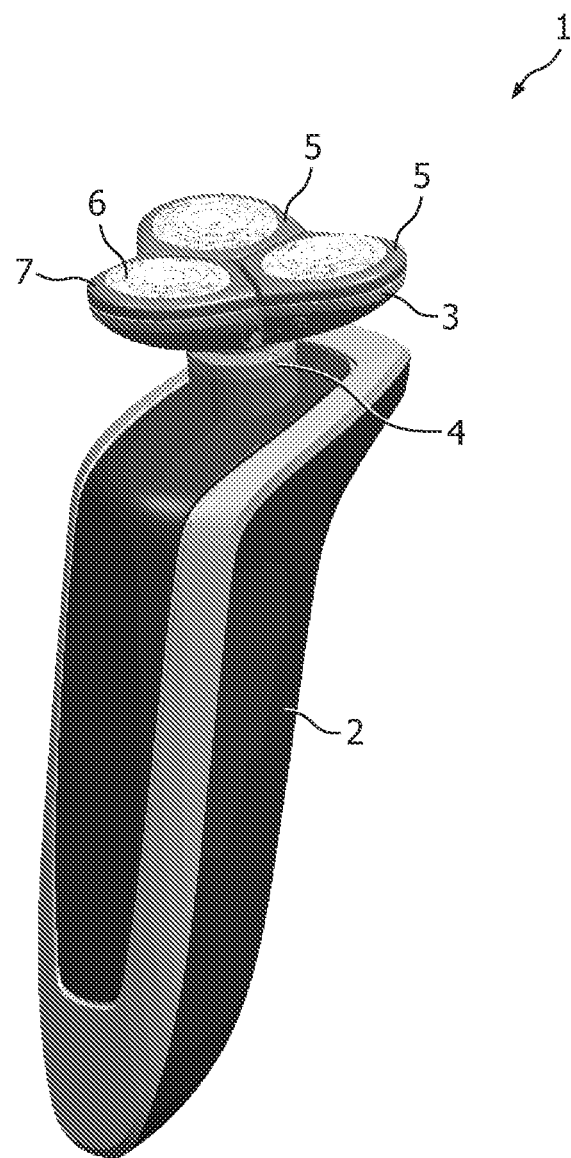
FIG. 1 is a perspective view of a shaving appliance according to the present invention, which comprises a shaving unit and a handle.
Figure 4:
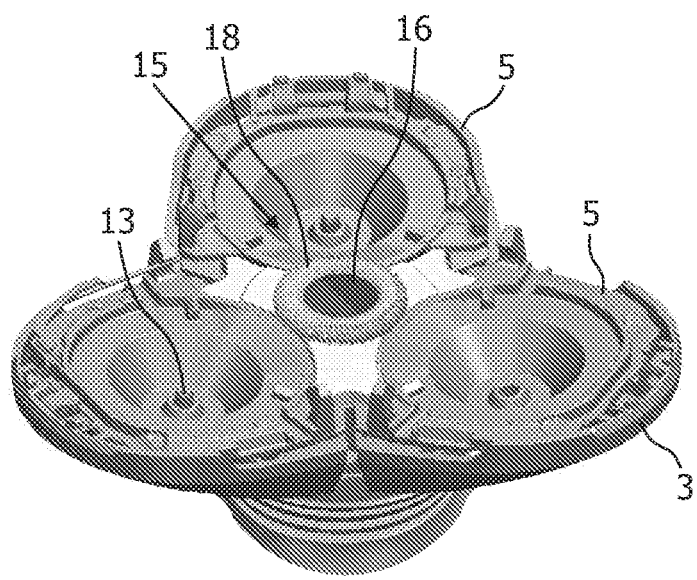
FIG. 4 is a perspective view of a second embodiment of the shaving unit of the shaving appliance according to the present invention, wherein a number of components of the shaving unit are omitted for the sake of clarity.

FIG. 1 shows a shaving appliance 1 according to the present invention, and FIG. 4 provides a diagrammatic representation of the shaving appliance 1. In general, a shaving appliance is a hand-held device which is suitable to be used for removing hairs from skin by performing an action commonly known as shaving, which is cutting through hairs at a position close to the skin. In view thereof, the shaving appliance 1 comprises a handle 2 for allowing a user to take hold of the shaving appliance 1, and a shaving unit 3, which is suitable to contact an area of skin having hairs to be shaved off. The shaving unit 3 is connected to the handle 2 through a central shaft member 4, wherein the connection of the shaving unit 3 to the handle 2 may be detachable.

Figure 2:
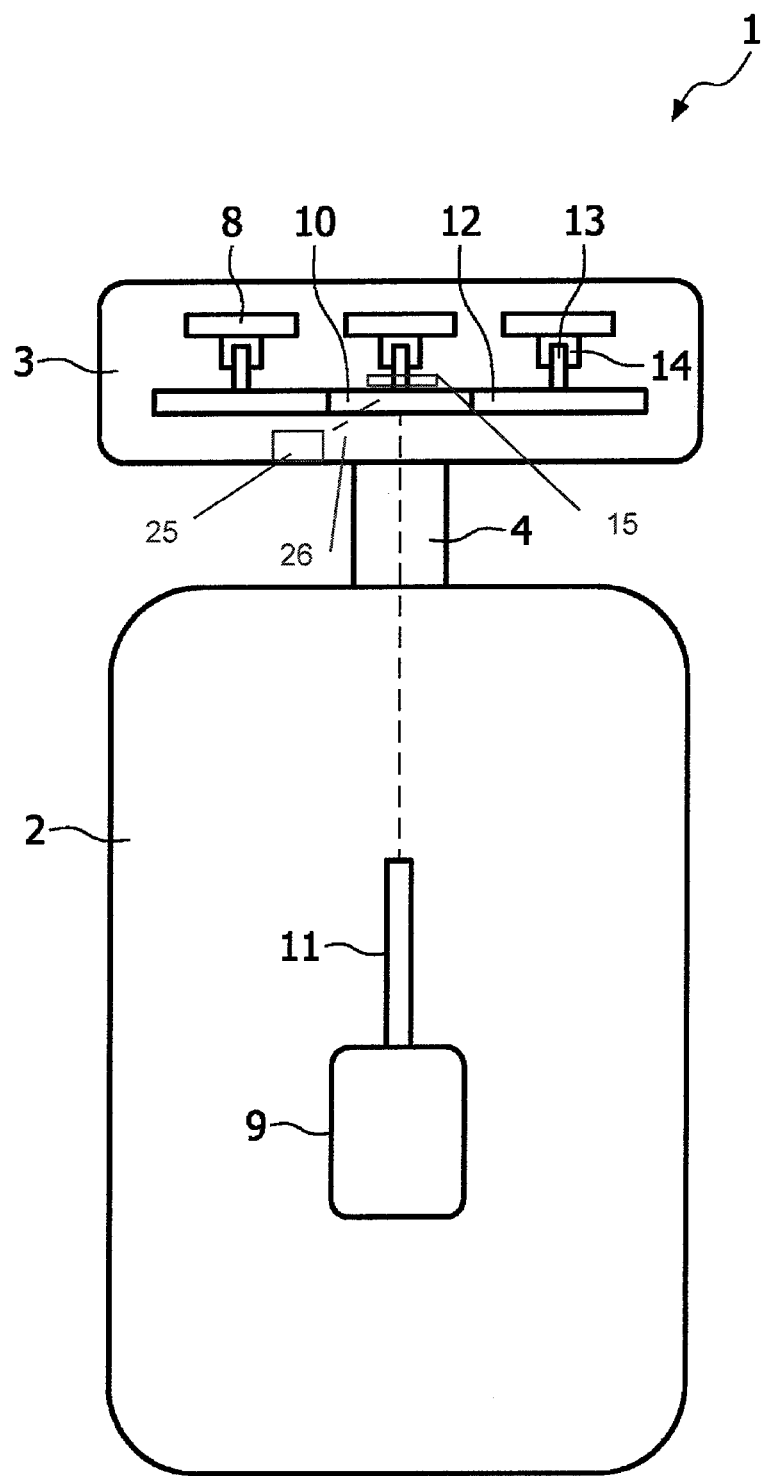
FIG. 2 diagrammatically shows a number of components of the shaving appliance as shown in FIG. 1.

In FIGS. 1 and 2, the shaving appliance 1 is shown in a typical orientation, namely an orientation in which a side of the shaving appliance 1 where the shaving unit 3 is present extends upwards. In the following, when words like "above" and "under" are used, it is assumed that the shaving appliance 1 is in this orientation. In any case, that does not alter the fact that the shaving appliance 1 may be used in any suitable orientation.

In the shown example, the shaving unit 3 comprises three shaving elements 5, which are arranged in a triangle formation. Within the scope of the present invention, the number of shaving elements 5 may be chosen freely, and may therefore also be less than three or more than three. For the sake of completeness, it is noted that each of the shaving elements 5 may be arranged so as to be movable to a certain extent, so as to facilitate following a contour of an area of skin to be shaved. For example, the shaving elements 5 may be pivotable, to a limited extent, with respect to the central shaft member 4.

Each shaving element 5 comprises a cap 6, which is arranged at a top side of the shaving element 5, and which is held in a ring-shaped cap holder 7, and which has a plurality of holes for letting through hairs to be shaved off. Right underneath the cap 6, on the inside of the shaving element 5, a cutting member 8 is rotatably arranged. The cutting member 8, which is only diagrammatically shown in FIG. 2, may have a design known per se, according to which the cutting member 8 comprises a disc and cutters which are arranged along a circumference of the disc. During operation of the shaving appliance 1, the disc of the cutting member 8 is rotated, and hairs extending through the holes in the cap 6 are cut off when they are hit by a cutter of the cutting member 8.

For the purpose of driving the cutting members 8, the shaving appliance 1 comprises a number of components, which are diagrammatically shown in FIG. 2, and which will be described in the following. In particular, the shaving appliance 1 comprises a motor 9, which is located in the handle 2. In the shaving unit 3, at a central position, a gear wheel 10 is arranged, which will hereinafter be referred to as primary gear wheel 10. The primary gear wheel 10 is coupled in any suitable manner to an output shaft 11 of the motor 9, which is a primary drive shaft 11 to the gear wheel 10. In FIG. 2, the coupling of the primary gear wheel 10 to the primary drive shaft 11 is diagrammatically depicted by means of a dashed line.

Each shaving element 5 accommodates a gear wheel 12, which is in engagement with the primary gear wheel 10. In the following, the gear wheels 12, which are located inside the shaving element 5, will be referred to as secondary gear wheels 12. A drive shaft 13 for driving the cutting member 8, which will hereinafter be referred to as secondary drive shaft 13, extends from each secondary gear wheel 12, and the cutting member 8 is coupled to the secondary drive shaft 13 through a suitable coupling member 14.

When the shaving appliance 1 is operated, the motor 9 is in an activated condition, as a result of which the primary drive shaft 11 and the primary gear wheel 10 coupled to the primary drive shaft 11 are rotated about a central rotation axis. As the primary gear wheel 10 is in engagement with the secondary gear wheels 12, the rotation of the primary gear wheel 10 about the central rotation axis causes rotations of the secondary gear wheels 12 about their respective rotation axes. Consequently, due to the fact that each cutting member 8 is coupled to a secondary gear wheel 12 through a secondary drive shaft 13 and a coupling member 14, rotations of the cutting members 8 are realized. When a user of the shaving appliance 1 moves the shaving unit 3 across an area of skin, hairs extending through the holes in the caps 6 of the shaving elements 5 are cut off by the cutters of the cutting members 8.

Figure 3:
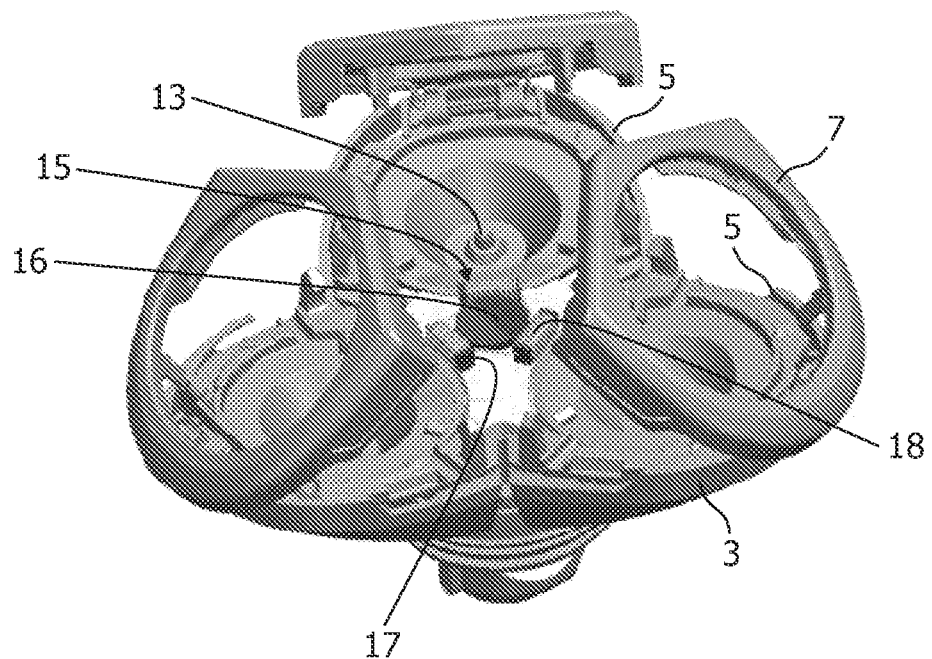
FIG. 3 is a perspective view of a first embodiment of the shaving unit of the shaving appliance according to the present invention, wherein a number of components of the shaving unit are omitted for the sake of clarity.

In FIG. 3, a first embodiment of the shaving unit 3 is shown, wherein a number of components of the shaving unit 3, including the caps 6 and the cutting members 8, are omitted for the sake of clarity. For the sake of completeness, it is noted that FIG. 3 shows that the cap holders 7 are hingably arranged in the shaving unit 3, wherein the cap holders 7 are movable between an opened position as shown in this Figure and a closed position as shown in FIG. 1. When the cap holder 7 of a particular shaving element 5 is in the opened position, the cap 6 and the cutting member 8 of that shaving element 5 may be removed, which may be useful for cleaning purposes, for example.

According to the present invention, the shaving unit 3 is equipped with means 15 for generating electric energy at the location of the shaving unit 3. It is advantageous to have such means 15 at a location inside the shaving unit 3, as this allows having one or more electric components 25 at the location of the shaving unit 3 as shown in FIG. 2, without a need for an external electric connection, which might be a connection towards the handle 2. Examples of electric components which may be located in the shaving unit 3 are cleaning LEDs for emitting ultraviolet rays, components for retaining and releasing the cap holder 7, micro heating components, micro cooling components, a light source in order to visualize a rotating cutting member 8 in a stroboscopic manner, a light source in order to visualize a cleaning process of the shaving unit 3 which is performed by using cleaning fluid, components suitable to be used at locations where drying of difficult-to-reach areas needs to be performed, and integrated circuits (ICs) for wireless communication purposes from the shaving unit 3 to the handle 2 or a device for subjecting the unit 3 to a cleaning action.

In general, according to the present invention, at least one component of the means 15 for generating electric energy is coupled to at least one component which serves for driving the cutting members 8, and which is located inside the shaving unit 3. In the shown examples, the means 15 for generating electric energy comprise a permanent magnet 16 which is mounted on the primary gear wheel 10. For example, the magnet 16 can be insert molded in the primary gear wheel 10. Besides the magnet 16, the means 15 for generating electric energy comprise at least one electric coil 18. It is well-known that electric energy can be generated by subjecting a coil to an alternating magnetic field, on the basis of a physical process called induction. In the shaving unit 3, the alternating magnetic field is obtained by virtue of the rotatably arranged magnet 16 which is connected to the primary gear wheel 10.

In the example as illustrated by FIG. 3, the permanent magnet 16 is surrounded by three other permanent magnets 17, wherein each of these magnets 17 extends through an electric coil 18. When the shaving appliance 1 is operated, and the primary gear wheel 10 and the magnet 16 arranged thereon are rotating, the coils 18 are subjected to an alternating magnetic field, as a result of which electric energy is generated. This electric energy may be used for operating one or more electric components through a connection 26 (FIG. 2) of these components to the coils 18. It is noted that the way in which electric energy is generated in the first embodiment of the shaving unit 3 is comparable to the way in which an electric motor having a rotor surrounded by a number of stators is operated to generate electric energy.

Figure 5:
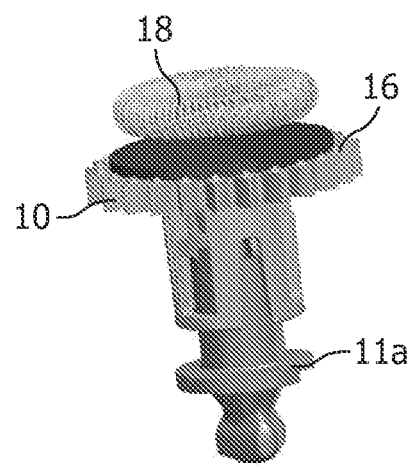
FIG. 5 is a perspective view of an assembly of a drive shaft end portion, a central gear wheel, a permanent magnet and an electric coil, which is part of the shaving unit as shown in FIG. 4.

FIG. 4 serves to illustrate another example, namely an example in which a single coil 18 is provided having an overall angular shape. The coil 18 is arranged right above the gear wheel 10 and the magnet 16, and its diameter is in the same order as the diameter of the magnet 16. FIG. 5 shows an assembly of the primary gear wheel 10, the magnet 16, the coil 18, and a drive shaft end portion 11a on which the gear wheel 10 is mounted.

Figure 6:
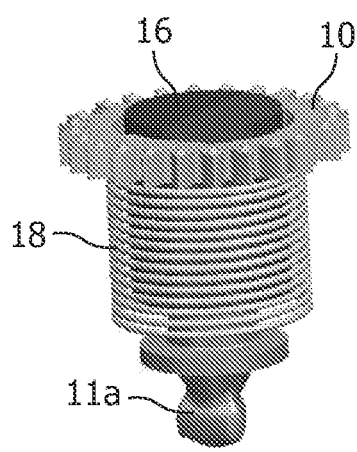
FIG. 6 shows an alternative of the assembly as shown in FIG. 5.
Figure 7:
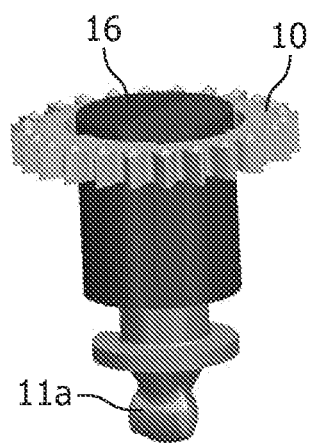
FIG. 7 shows the assembly as shown in FIG. 6, wherein the electric coil is omitted for the sake of clarity.

Yet another embodiment of the means 15 for generating electric energy during operation of the shaving appliance 1 is illustrated by FIGS. 6 and 7. In the previous two examples, the permanent magnet 16 coupled to the primary gear wheel 10 is shaped like a disc. However, in this third example, the magnet 16 is shaped like a cylinder, as is clearly shown in FIG. 7. The coil 18 which is part of this embodiment of the means 15 for generating electric energy is arranged such as to encompass the magnet 16. In other words, an arrangement is obtained in which the magnet 16 extends through the coil 18, as is clearly shown in FIG. 6.

Besides the shown examples of the means 15 for generating electric energy at the location of the shaving unit 3, other examples are feasible as well. In any case, it is an important achievement of the present invention that it is possible to have an autonomous source for supplying electric energy to one or more electric components inside the shaving unit 3, without there being any need for a connection to an external energy source, i.e. an energy source which is not arranged inside of the shaving unit 3. An advantageous aspect of the present invention is that the generation of electric energy is based on the movement which is needed to drive the cutting members 8 of the shaving unit 3, so that an embodiment of the means 15 for generating electric energy may be compact and does not need additional drive components.

It will be clear to a person skilled in the art that the scope of the present invention is not limited to the examples discussed in the foregoing, but that several amendments and modifications thereof are possible without deviating from the scope of the present invention as defined in the attached claims. While the present invention has been illustrated and described in detail in the Figures and the description, such illustration and description are to be considered illustrative or exemplary only, and not restrictive. The present invention is not limited to the disclosed embodiments.

Variations to the disclosed embodiments can be understood and effected by a person skilled in the art in practicing the claimed invention, from a study of the Figures, the description and the attached claims. In the claims, the word "comprising" does not exclude other steps or elements, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope of the present invention.

In the foregoing, a shaving appliance 1 has been disclosed, which comprises a shaving unit 3 which has at least one movably arranged member 8 adapted to cut through hairs, and driving means 10, 11a, 12, 13 adapted to impose a movement on the cutting member 8, and which further comprises means 15 for generating electric energy at the location of the shaving unit 3. The means 15 for generating electric energy are associated with the driving means 10, 11a, 12, 13, and are adapted to employ movement of at least one movable member of the driving means 10, 11a, 12, 13 in a process of generating electric energy. In a practical embodiment, the means 15 for generating electric energy comprise a permanent magnet 16 and an electric coil 18, wherein the magnet 16 may be mounted on a movably arranged component of the driving means 10, 11a, 12, 13.

By having the means 15 for generating electric energy at a location inside the shaving unit 3, it is possible to have one or more electric components at a location inside the shaving unit 3 as well, since there is no need for an external electric connection for supplying these components with the electric energy that is required for their operation.

In general, the present invention relates to a domestic appliance and a functional action unit for use in such an appliance. Examples of a domestic appliance are a vacuum cleaner, a blender, a mixer, and a personal care appliance such as an electric toothbrush, a shaving appliance 1 as described, or any other hair removal appliance. In the case of a vacuum cleaner, electric energy may be generated at the location of the intake port, for example by means of a magnetic rotary propeller in a flow of air, wherein the electric energy may be applied for operating one or more LEDs for lighting the area to be cleaned. In the case of an electric toothbrush, the electric energy which is generated in the functional action unit during operation may be used for things like operating a LED for emitting ultraviolet light for performing a disinfecting function, indicating wear of brush hairs, and operating a Red/Green/Blue LED (RGB LED) for indicating contamination on the basis of color.

The invention claimed is:

1. A domestic appliance configured to cut hairs for performing a shaving process, comprising:
  a handle for being held by a user during the shaving process;
  a functional action unit mounted on the handle and configured to perform an action which is directly related to an intended function of the domestic appliance;
  at least one movably arranged member configured to cut through the hairs and located in the functional action unit; and
  an energy source configured to generate electric energy, wherein the handle encloses a power source configured to provide power to the movably arranged member, wherein the energy source is at a location of the functional action unit, and wherein the energy source is configured to generate the electric energy from movement of the at least one movably arranged member,
  wherein the energy source comprises a permanent magnet and an electric coil.

2. The domestic appliance according to claim 1, wherein both the at least one movably arranged member for performing the action which is directly related to the intended function of the domestic appliance and a driver configured to impose a movement on the at least one movably arranged member are located in the functional action unit, and wherein the energy source is configured to generate the electric energy from movement of at least one movable member of the driver.

3. The domestic appliance according to claim 2, wherein the driver comprises a rotatably arranged gear wheel, and wherein a moving member of the energy source is attached to the gear wheel.

4. The domestic appliance according to claim 3, wherein the functional action unit further comprises at least two functional action members, wherein the gear wheel has a central position between the at least two functional action members and serves for driving the at least two functional action members.

5. The domestic appliance according to claim 1, further comprising at least one electric component which requires energy for operation and which is located in the functional action unit, wherein the at least one electric component is connected to the energy source and uses the electric energy generated by said energy source for operation of the at least one electric component.

6. The domestic appliance according to claim 1, further comprising a drive shaft protruding from the handle and extending into the functional action unit.

7. A unit for a domestic appliance, said unit being configured to perform an action which is directly related to an intended function of the domestic appliance, said unit comprising:
  at least one movably arranged member configured to be driven by a motor located external to the unit; and
  an energy source configured to generate electric energy, wherein the energy source is configured to generate the electric energy from movement of the at least one movably arranged member,
  wherein the energy source comprises a permanent magnet and an electric coil.

8. The unit according to claim 7, wherein the at least one movably arranged member is configured to perform action which is directly related to the intended function of the domestic appliance in which the unit is to be used, and wherein the unit further comprises a driver configured to impose a movement on the at least one movably arranged member, wherein the energy source is configured to generate the electric energy from movement of at least one movable member of the driver.

9. The unit according to claim 8, wherein the driver comprises a rotatably arranged gear wheel, and wherein the at least one movably arranged member is attached to the gear wheel.

10. The unit according to claim 9, further comprising at least two functional action members, wherein the gear wheel has a central position between the at least two functional action members and serves for driving the at least two functional action members.

11. The unit according to claim 7, further comprising at least one electric component which requires energy for operation, wherein the at least one electric component is connected to the energy source and uses the electric energy generated by said energy source for operation of the at least one electric component.

12. The unit according to claim 7, wherein the at least one movably arranged member is configured to cut through hairs.

13. The unit of claim 7, wherein the permanent magnet is mounted on a gear wheel of the unit and the coil is mounted on the permanent magnet, and wherein the permanent magnet and the coil have a same diameter.

14. A domestic appliance comprising:
  a functional action unit configured to perform an action which is directly related to an intended function of the domestic appliance;
  a motor located in a further unit external to the functional action unit and coupled to the functional action unit, wherein the motor is configured to operate the functional action unit to perform the action;
  at least one movably arranged member which is located in the functional action unit;
  an energy source configured to generate electric energy, wherein the energy source is at a location of the functional action unit, and wherein the energy source is configured to generate the electric energy from movement of the at least one movably arranged member,
  wherein the energy source comprises a permanent magnet and an electric coil.

15. The domestic appliance of claim 14, wherein the further unit is a handle of the domestic appliance connected to the functional action unit though a shaft member.

16. The domestic appliance of claim 14, wherein the permanent magnet is mounted on a gear wheel of the functional action unit and the coil is mounted on the permanent magnet, and wherein the permanent magnet and the coil have a same diameter.

17. The domestic appliance of claim 14, wherein the permanent magnet is cylindrical and extends through the coil.

18. The domestic appliance of claim 14, wherein the energy source further comprises three permanent magnets that surround the permanent magnet, and three coils, wherein each of the three permanent magnets extends through a respective coil of the three coils.

* * * * *